United States Patent [19]

Ueda

[11] 4,335,261

[45] Jun. 15, 1982

[54] PROCESS FOR PURIFYING MACROCYCLIC KETONES

[75] Inventor: Yoichiro Ueda, Ohimachi, Japan

[73] Assignee: Daicel Chemical Industries, Ltd., Osaka, Japan

[21] Appl. No.: 274,682

[22] Filed: Jun. 17, 1981

[30] Foreign Application Priority Data

Jul. 18, 1980 [JP] Japan .................................. 55-98258

[51] Int. Cl.[3] .............................................. C07C 45/83

[52] U.S. Cl. .................................... 568/366; 568/346; 203/95

[58] Field of Search ........................ 568/366, 410, 346; 203/54, 62, 95

[56] References Cited

U.S. PATENT DOCUMENTS 3,265,592 8/1966 Van der Weil ..................... 568/410

3,276,973 10/1966 Burmaster et al. ................. 568/410

3,378,466 4/1968 Coltharp et al. ...................... 203/95

FOREIGN PATENT DOCUMENTS 1282209 12/1961 France ............................... 568/366

OTHER PUBLICATIONS

Gromoglasor et al., Chem. Abst., vol. 84, #1212502, (1976).

*Primary Examiner*—Natalie Trousof
*Assistant Examiner*—ames H. Reamer
*Attorney, Agent, or Firm*—Blanchard, Flynn, Thiel, Boutell & Tanis

[57] ABSTRACT

A macrocyclic ketone having a 15- to 17-membered ring is produced from an $\alpha,\omega$-long chain dicarboxylic acid ester by the Dieckmann condensation reaction, followed by hydrolysis/decarboxylation reaction and then purification. The macrocyclic ketone is purified by subjecting the ketone to steam distillation in the presence of a non-volatile base.

9 Claims, No Drawings

PROCESS FOR PURIFYING MACROCYCLIC KETONES

The present invention relates to a process for purifying macrocyclic ketones useful as musk perfume ingredients.

Musk, found in a natural material, comprises macrocyclic compounds. It has a high value in the perfumery field. Because musk is very expensive, various synthesis methods for preparing same have been studied. One of the synthesis methods comprises the Dieckmann condensation (base-catalyzed intramolecular cyclization) of $\alpha,\omega$-long chain dicarboxylic acid esters. For example, it has been known that cyclopentadecanone can be obtained by subjecting diethyl thapsate to the Dieckmann condensation whereby to obtain ethyl 2-oxocyclopentadecane carboxylate, then heating that compound with hydrochloric acid for a long period of time to effect hydrolysis and decarboxylation thereof. The resulting product is purified by extraction with an ether and distillation, whereby to obtain the desired cyclopentadecanone [N. J. Leonard, C. W. Schimelpfenig Jr., Org. Chem., 23, 1708 (1958)].

In the same manner as described above, ethyl 2-oxocycloheptadeca-10-ene carboxylate is obtained by the Dieckmann condensation of diethyl octadeca-9-ene diacid, the product is hydrolyzed with hydrochloric acid and decarboxylated in the same manner as described above and a xylene layer containing the product is subjected to distillation to obtain 9-cycloheptadecen-1-one (civetone) (see the specification of Japanese Patent Laid-Open No. 118447/1977).

The commercial value of the final, purified, synthesis product, for use in the field of perfumes, is determined by its fragrance. Components giving off unwanted or offensive smells may be contained therein in only a very small amount and they are scarcely detectable by instrumental analysis. The products are, therefore, tested for offensive smells organoleptically by a panel of very skillful, odor-sensitive test persons. In view of those circumstances, particularly strict operational conditions are required for synthesizing ingredients suitable for use in perfumes.

It has been found that the conventional processes for the isolation of the desired macrocyclic ketone product by hydrolysis with hydrochloric acid and decarboxylation, followed by distillation of the organic solvent solution, have two problems.

One of the problems is that the hydrolysis rate is low and, therefore, the hydrolysis of the ester is incomplete even after treatment for a long period of time. The other problem is that the quality of the resulting macrocyclic ketone is insufficient with respect to the fragrance for the musk perfume desired.

It is also known that cyclodecanone is obtained by the alkali hydrolysis and decarboxylation of methyl 2-oxocyclodecanone carboxylate, followed by purification by extraction with ether and distillation. The Dieckmann method is not employed in that process, unlike the process of the present invention (Org. Syntheses, Coll, Vol. V. page 277). If that process is applied to a macrocyclic Dieckmann condensation product, the problem of the slow hydrolysis rate is solved, but the quality (fragrance) of the final product is still poor. It has been found that the fragrance thereof cannot be improved by any of the conventional purification processes, such as re-distillation, recrystallization and distillation followed by recrystallization. This is the most serious problem in the synthesis according to the Dieckmann condensation.

The inventor has discovered the above-mentioned problem in the production of synthetic macrocyclic ketones by the Dieckmann method. After investigations made for the purpose of solving that problem, the inventor has completed the present invention.

The present invention provides a purification procedure, employed in the production of a synthetic macrocyclic ketone having a 15- to 17-membered ring, prepared from an $\alpha,\omega$-long chain dicarboxylic acid ester by the Dieckmann condensation reaction, followed by hydrolysis/decarboxylation reaction and purification, which purification procedure for purifying the macrocyclic ketone is characterized by the fact that the macrocyclic ketone is subjected to steam distillation, in the presence of a non-volatile base.

In the purification procedure according to the present invention, the treatment (C) of effecting steam distillation, in the presence of non-volatile base, is critical. This treatment can be combined with an extractive distillation treatment (A) and/or a methanol recrystallization treatment (B), effected before or after the steam distillation treatment (C). Among these combinations of treatments, the combination of treatment (C) with treatment (B) is most effective.

The most important condition for improving the desired fragrance of a musk perfume is to employ the purification treatment (C) in the present invention. In addition to the above combination of treatments, additional purification treatments generally employed in the field of preparing perfume ingredients, such as simple steaming, aeration, neutralization and washing, can be employed as the occasion demands.

Embodiments of the purification treatments to be combined with the treatment (C), according to the present invention, will be described below: In treatment (A), 20–40 parts by volume of hexane are used for the extraction, per one part by volume of the crude macrocyclic ketone. Hexane is expelled from the extract under ambient pressure or reduced pressure and then the residue is subjected to distillation by means of a flash, thin-film evaporator, at a temperature of 125°–140° C., under a reduced pressure of 0.2–0.4 Torr. In treatment (B), one part by weight of the crude macrocyclic ketone is dissolved in 1–2 parts by weight of methanol, the solution is cooled to −5° C. to −10° C. and the thus-precipitated solids are filtered out.

In treatment (C), according to the process of the present invention, a non-volatile base is added to (or incorporated in) the crude macrocyclic ketone so as to maintain the pH of the aqueous phase in a suitable range and then the distillation is effected, while steam is introduced (directly injected) therein, at a still pot temperature of 120° to 150° C., under atmospheric pressure.

The non-volatile bases used in the process of the present invention include non-volatile strong bases, weak bases and salts of weak acids with strong bases. As the strong bases, there can be mentioned alkali metal hydroxides, such as sodium hydroxide and potassium hydroxide. As the weak bases, there can be mentioned weakly alkaline metal hydroxides, such as magnesium hydroxide and aluminum hydroxide. As the salts of weak acids with strong bases, there can be mentioned alkali metal salts of organic acids, such as sodium acetate, potassium acetate, sodium propionate and potassium propionate, and alkali metal salts of mineral acids, such as sodium phosphate, potassium phosphate, sodium carbonate and potassium carbonate. Among those bases, sodium acetate and potassium acetate are particularly preferably used.

The amount of the base used is suitably controlled to attain a suitable pH (common logarithm of the reciprocal of the molar concentration of hydrogen ion) in the aqueous phase in the solution, in which solution the base is present in only the aqueous phase. Namely, the amount is controlled to attain a pH in the range of about 7.5 to 10, preferably about 8 to 9.5. If the pH is up to 7 (neutral or acidic), the quality of the resulting macrocyclic ketone is unsatisfactory with respect to the fragrance desired for a musk-like perfume. If the pH is above 10 (strongly alkaline), undesirable side reactions, such as condensation reactions, also occur whereby unfavorably to reduce the yield of the desired product, although the fragrance is almost satisfactory.

The compounds which can be treated by the process of the present invention are crude macrocyclic ketones containing 15 to 17 carbon atoms in the ring, obtained by a reaction step (Dieckmann method) as will be described below, such as cyclopentadecanone and 9-cycloheptadecen-1-one (civetone). This treatment is as follows:

(I) An $\alpha,\omega$-long chain dicarboxylic acid ester, as the starting material, is subjected to the Dieckmann condensation, in the presence of tert-butoxy potassium, as the condensing agent, in dry xylene, as a solvent, under a nitrogen atmosphere, at the reflux temperature of xylene, for 20 to 30 hours, whereby to obtain a macrocyclic (keto) carboxylic acid ester.

(II) Then, the concentrated residue is subjected to the hydrolysis/decarboxylation reaction, in the presence of about 50% aqueous sodium hydroxide, as a saponifying agent, in methanol, as a solvent, at the reflux temperature of methanol, for 3 to 5 hours, whereby to obtain a crude macrocyclic ketone.

Since an alkali is used in above reaction step (II), the reaction velocity becomes higher and the reaction time becomes shorter in comparison with those employed in conventional processes wherein hydrochloric acid is used and, in addition, the final product has an improved fragrance. Further, the alkali can be used, directly or after a treatment, for example, reaction with acetic acid to form the corresponding alkali metal acetate, as the non-volatile base in the subsequent purification step. This also is an advantage of the present invention.

By carrying out the process of the present invention, there can be obtained macrocyclic ketones having a satisfactory commercial value, as desired for musk-like perfumes, and which are completely free of the smell of the solvent or a burnt smell, unlike macrocyclic ketones obtained by conventional purification processes. It is thus believed that the process of the present invention has a great industrial value.

The following examples further illustrate the present invention. The invention is by no means limited to the subject matter of the examples. The components were determined by gas chromatographic analysis.

EXAMPLE 1

(Cyclopentadecanone)

220 g of ethyl thapsate having a purity of 98%, as the starting material, was subjected to the Dieckmann reaction, in the presence of tert-butoxy potassium, as the condensing agent, in anhydrous xylene, as the solvent, according to the method disclosed in J. Org. Chem., 23, 1708 (1958). In this step, the starting ethyl ester was dissolved in 1.98 Kg of xylene to obtain a homogeneous solution. The solution was added dropwise to the reaction mixture maintained under a nitrogen atmosphere, under heating to the reflux temperature of xylene (140°-150° C.), for 20.5 hours. According to the teaching of the above publication, an alcohol/xylene mixture was taken out from the system by distillation, at substantially the same rate as the rate of addition of the solution of the starting ester in xylene. After completion of the addition of the starting ester, the heating was continued to distill out a part of xylene used as the solvent from the reaction system. Then, the reaction system was cooled to 17° C. and was neutralized with 245 g of 33% aqueous acetic acid solution. The insoluble suspended matter was allowed to remain in the reaction system or, in other words, it was not filtered out. The remaining xylene was completely distilled out at an oil bath temperature of 75° C. under a reduced pressure of 20 Torr whereby to obtain 405 g of a concentrated residue. The residue was mixed with 360 g of methanol and 200 g of 50% aqueous potassium hydroxide solution and the mixture was subjected to a hydrolysis/decarboxylation reaction, under mild reflux of the solvent 70°-80° C.). After heating and reflux for three hours, the reaction system was cooled to room temperature. 64 g of glacial acetic acid was added thereto. The major part of the alcohol was distilled out by simple distillation whereby to obtain 550 g of a concentrated residue. The pH of the aqueous layer was 8.0. The concentrated residue was transferred into a 1 liter three-neck flask. The flask was provided with a steam-introducing port, a thermometer, a distillation head and a cooling tube connected with the distillation head. Steam was directly injected into the flask at a rate of 1.1 Kg/hr. The steam distillation was continued while the internal temperature was elevated gradually from 127° C. to 152° C. by external heating by means of an oil bath. Ten (10) fractions of the distillate were recovered. The cyclopentadecanone in each fraction was filtered out whereby to separate the same from the water and then it was air-dried at room temperature for 24 hours. Eight fractions (78.9 g in total), excluding the first and the second fractions (1.0 g and 3.3 g, respectively), having a strong smell of the solvent were dissolved in the same weight of methanol. The resulting solution was cooled to −5° C. The colorless solid thus precipitated was filtered out and then dried at 40° C. under a reduced pressure of 20 Torr for 24 hours to remove the solvent, thereby obtaining 67.8 g of a crystalline sample of cyclopentadecanone having a purity of 99.0%. The fragrance was examined by a panel comprising 9 members. A set of samples comprising the above crystalline sample and two standard cyclopentadecanone samples was subjected to the test, particularly as regards the acid smell and the solvent (xylene) smell. The results were judged to be good or bad. The fragrance of the sample obtained in this example was judged to be good by 7 members and bad (due to the smell of the solvent) by two members.

COMPARATIVE EXAMPLE 1

11.5 g of ethyl thapsate having a purity of 99.3% was subjected to the Dieckmann condensation reaction and hydrolysis/decarboxylation reaction in the same manner as described in Example 1. The resulting cyclopentadecanone was separated out by extraction with hexane. By extraction with 200 ml of hexane, which was repeated two times, 6.41 g of an extract was obtained. The extract was subjected to distillation, at 140° C., under a reduced pressure of 0.4 Torr, whereby to obtain 4.38 g of cyclopentadecanone having a purity of 99.0% and 1.49 g of a residue. The cyclopentadecanone sample was pulverized into flakes and was air-dried at room temperature for 24 hours. The fragrance of the product was evaluated in the same manner as described in Example 1. All nine members of the panel judged the sample to be bad.

4.0 g of the flaky cyclopentadecanone sample was recrystallized from 7 g of methanol in a conventional manner whereby to obtain 2.5 g of a crystalline sample. The sample was dried at 40° C., under reduced pressure of 20 Torr, for 24 hours, to remove the solvent therefrom. The fragrance thereof was evaluated in the same manner as described above. All nine members of the panel judged the sample to be bad.

EXAMPLE 2

153 g of ethyl thapsate having a purity of 98% was subjected to the Dieckmann condensation reaction and the hydrolysis/decarboxylation reaction in the same manner as described in Example 1. Cyclopentadecanone was separated out by the extraction with hexane. By extraction with 2 liters of hexane, which was repeated twice, 92.0 g of an extract was obtained. The extract was subjected to distillation, at 140° C., under reduced pressure of 0.4 Torr, whereby to obtain 73 g of cyclopentadecanone having a purity of 98.9% and 16.1 g of a residue. 70 g of the cyclopentadecanone sample was taken, mixed with 70 g of water and 14 g of potassium acetate, in the same device and in the same manner as described in Example 1 (the aqueous layer had a pH of 8.5) and then was subjected to steam distillation whereby to obtain seven fractions each having substantially the same weight (68.2 g in total). Each fraction was air-dried at room temperature for 24 hours. The fragrance of the product was evaluated in the same manner as described in Example 1. The first and the second fractions were judged to be bad by all the members of the panel. The third to the seventh fractions were judged to be good by six members and judged to be bad by three members.

COMPARATIVE EXAMPLE 2

40.0 g of ethyl thapsate having a purity of 99% was subjected to the Dieckmann condensation reaction and the hydrolysis/decarboxylation reaction in the same manner as described in Example 1. The resulting cyclopentadecanone was separated out by extraction with hexane. By extraction with one liter of hexane, which was repeated twice, 22.4 g of an extract was obtained. The extract was subjected to the distillation, at 140° C., under reduced pressure of 0.4 Torr, whereby to obtain 13.8 g of cyclopentadecanone having a purity of 96.9%, and 7.5 g of a residue. The entire cyclopentadecanone sample was placed in a 500 ml three-neck flask, mixed with only 20 g of water (the aqueous layer having a pH of 6.8) and was then subjected to steam distillation in the same manner as described in Example 1 whereby to obtain two fractions each having substantially the same amounts (13.6 g). After air-drying at room temperature for 24 hours, the fragrance of the product was judged in the same manner as described in Example 1. All nine members of the panel judged the product to be bad.

COMPARATIVE EXAMPLE 3

70 g of a cyclopentadecanone sample (purity: 97.2%) was subjected to steam distillation after adjusting the pH of the aqueous layer to 11 with 50% aqueous sodium hydroxide solution, in the same device and in the same manner as described in Example 1. The total amount of the distillate was 61.3 g. The purification yield of cyclopentadecanone was about 5% lower than that obtained in Example 2.

EXAMPLE 3

[Synthesis of 9-cycloheptadecen-1-one (civetone)]

11.0 g of diethyl ester of octadeca-9-ene diacid having a purity of 88.5%, as a starting material, was subjected to the Dieckmann reaction, in the presence of potassium tert-butoxide, as the condensing agent, in dry xylene, as the solvent, according to the method disclosed in J. Org. Chem., 23, 1708 (1958), in the same manner as described in Example 1. In this step, the starting ester was dissolved in 161 g of xylene to obtain a homogeneous solution. The solution was added dropwise and continuously to the reaction mixture maintained under a nitrogen atmosphere, under heating to a reflux temperature of xylene (140°–150° C.), for 6.5 hours. An ethyl alcohol/xylene mixture was taken out from the system by distillation at substantially the same rate as the rate of addition of the solution of the starting ester in xylene. After completion of the addition of the starting ester, the heating was continued to distill out a part of xylene, used as the solvent, from the reaction system. Then, the reaction system was cooled to 30° C. and neutralized with 18.0 g of 33% aqueous acetic acid solution. The thus-produced solid insoluble in xylene was filtered out and the filtrate was concentrated by means of a rotary evaporator to obtain 12.5 g of a viscous, light yellow liquid product.

The liquid product was subjected to the hydrolysis/-decarboxylation reaction.

In this step, the entire liquid product was heated together with a mixture of 5.0 g of solid potassium hydroxide, 5.0 g of water and 17.9 g of methanol, at the reflux temperature of the solvent (70°–80° C.), for three hours. Then, the reaction system was cooled to room temperature and 3.2 g of glacial acetic acid was added. The major part of the alcohol was distilled out by means of a rotary evaporator. 50 g of water was added to the concentrated residue. Extraction with 100 ml of hexane was repeated three times and the solvent was evaporated out whereby to obtain 6.1 g of an oily product (crude civetone). The oily product was subjected to distillation under a reduced pressure of 0.3 Torr to obtain 5.9 g of the main distillate.

The fragrance of the resulting main distillate was evaluated by the method described in Example 1. It was judged to be good by 7 members of the panel and bad by two members. After storing the sample for one month, the fragrance thereof was again judged. All members of the panel recognized an offensive smell. The sample had become colored yellow.

Separately, 5.0 g of the main distillate obtained by the reduced pressure distillation was mixed with 10 g of water and 0.3 g of sodium acetate (the pH of the aqueous layer being 9.1) and then was subjected to steam distillation whereby to obtain 4.85 g of an oily distillate. Water was evaporated out from the distillate under a reduced pressure of 0.3 Torr and the fragrance of the product was evaluated in the same manner as above. It was judged to be good by 7 members of the panel. The results were unchanged after storage of the sample for one month.

The embodiments of the invention in which an exclusive property or privilege is claimed are defined as follows:

1. In a process for preparing a macrocyclic ketone having from 15 to 17 carbon atoms in the ring by effecting base-catalyzed intramolecular cyclization of an $\alpha,\omega$-long chain aliphatic dicarboxylic acid ester according to the Dieckmann condensation reaction to form a macrocyclic keto carboxylic acid ester, followed by hydrolysis and decarboxylation to obtain a crude macrocyclic ketone and then by purification of said crude macrocyclic ketone, the improvement which comprises: the purification treatment comprises injecting open steam into the crude macrocyclic ketone, in the presence of a non-volatile base, to effect steam distillation and recovering the purified macrocyclic ketone as the distillate.

2. A process as claimed in claim 1 in which the purification treatment also comprises dissolving the crude macrocyclic ketone in hexane to obtain an extract containing the ketone, then removing hexane from the extract, then distilling the residue in a thin-film evaporator, at a temperature of 125° to 140° C., under a pressure of 0.2 to 0.4 Torr, whereby to recover the ketone.

3. A process as claimed in claim 1 in which the purification treatment also comprises dissolving the crude macrocyclic ketone in methanol to obtain a solution, then cooling said solution to from −5° to −10° C., filtering the solids and recovering the ketone from the solids.

4. A process as claimed in claim 1 in which the steam distillation is effected at a temperature of from about 120° to about 150° C., at atmospheric pressure.

5. A process as claimed in claim 1 in which said non-volatile base is selected from the group consisting of sodium hydroxide, potassium hydroxide, magnesium hydroxide, aluminum hydroxide, sodium acetate, potassium acetate, sodium propionate, potassium propionate, sodium phosphate, potassium phosphate, sodium carbonate and potassium carbonate.

6. A process as claimed in claim 1 in which said non-volatile base is sodium acetate or potassium acetate.

7. A process as claimed in claim 1 in which, in the hydrolysis and decarboxylation reaction, the macrocyclic keto carboxylic acid ester is dissolved in methanol and is contacted with an aqueous solution of an alkali metal hydroxide at the reflux temperature of the methanol until hydrolysis and decarboxylation is completed.

8. A process as claimed in claim 1 in which, during the steam distillation, the crude macrocyclic ketone is in contact with an aqueous liquid phase containing said non-volatile base, said aqueous phase having a pH in the range of from about 7.5 to about 10.

9. A process as claimed in claim 1 in which said macrocyclic ketone is cyclopentadecanone or 9-cycloheptadecen-1-one.

* * * * *